(12) United States Patent
Rycroft

(10) Patent No.: US 7,748,072 B2
(45) Date of Patent: Jul. 6, 2010

(54) TOOTHBRUSH

(75) Inventor: Kendall Peter Rycroft, 7251 Goldenrod Ct., Ooltewah, TN (US) 37363

(73) Assignee: Kendall Peter Rycroft, Alpharetta, GA (US)

( * ) Notice: Subject to any disclaimer, the term of this patent is extended or adjusted under 35 U.S.C. 154(b) by 1159 days.

(21) Appl. No.: 11/296,403

(22) Filed: Dec. 8, 2005

(65) Prior Publication Data

US 2006/0130253 A1 Jun. 22, 2006

Related U.S. Application Data

(60) Provisional application No. 60/634,108, filed on Dec. 8, 2004, provisional application No. 60/647,805, filed on Jan. 31, 2005.

(51) Int. Cl.
*A46B 15/00* (2006.01)
*A46B 9/04* (2006.01)
*F21V 33/00* (2006.01)

(52) U.S. Cl. .................. 15/105; 15/167.1; 362/109

(58) Field of Classification Search .............. 15/105, 15/22.1; 434/263; 353/43, 24, 96, 100, 35; 362/253, 804, 109; *A46B 13/02*
See application file for complete search history.

(56) References Cited

U.S. PATENT DOCUMENTS

| | | | | | |
|---|---|---|---|---|---|
| 2,778,043 | A | * | 1/1957 | Arf | ............... 15/28 |
| 4,476,604 | A | * | 10/1984 | White et al. | ............. 15/105 |
| 4,779,173 | A | * | 10/1988 | Carr et al. | ............. 362/109 |
| 6,106,294 | A | * | 8/2000 | Daniel | ............. 433/216 |
| 6,202,242 | B1 | * | 3/2001 | Salmon et al. | ............. 15/22.1 |
| 6,606,755 | B1 | * | 8/2003 | Robinson et al. | ............. 15/105 |
| 2003/0205492 | A1 | * | 11/2003 | Ferber et al. | ............. 206/362.2 |
| 2004/0143920 | A1 | * | 7/2004 | Nanda | ............. 15/105 |

* cited by examiner

*Primary Examiner*—Joseph J Hail, III
*Assistant Examiner*—Jamal Daniel

(57) ABSTRACT

A toothbrush includes a head assembly with bristles, a base assembly, and a connector which connects the two. A battery and light assembly are disposed in the connector and base assembly, and a power button switch turns the power to a light source "ON/OFF". The base assembly includes a transparent lens portion at the distal end, through which a light beam from the light source shines when the switch is turned ON. The light beam can project a picture or icon on a slide through the lens portion onto a remote surface. The slide can be permanently fixed in the base assembly or interchangeable. A timer is connected to the batteries, light source, and switch, and allows the light source to turn on for a predetermined period of time. Alternatively, the base assembly contains at least one indicator light which indicates how long the light source has been ON.

16 Claims, 3 Drawing Sheets

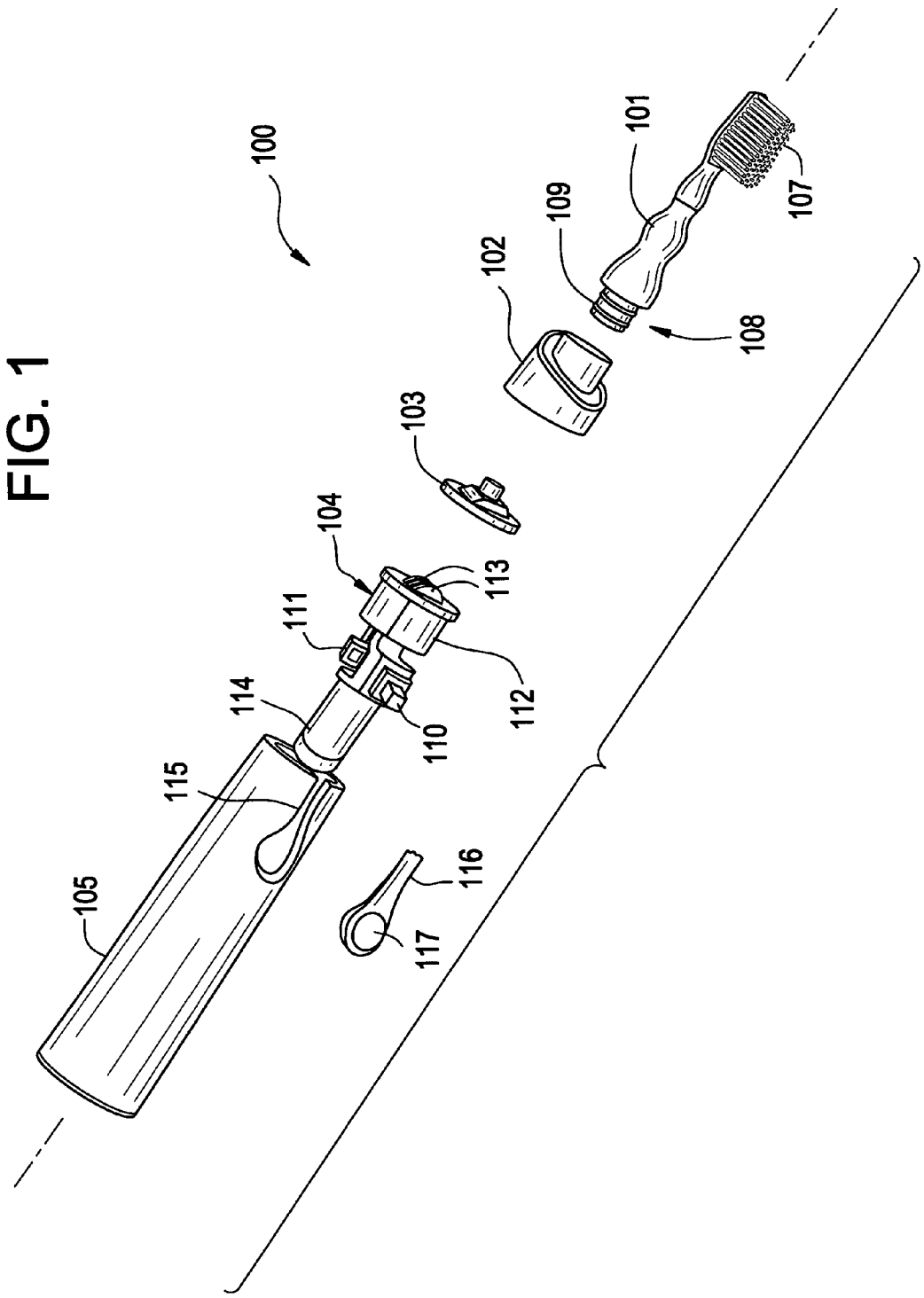

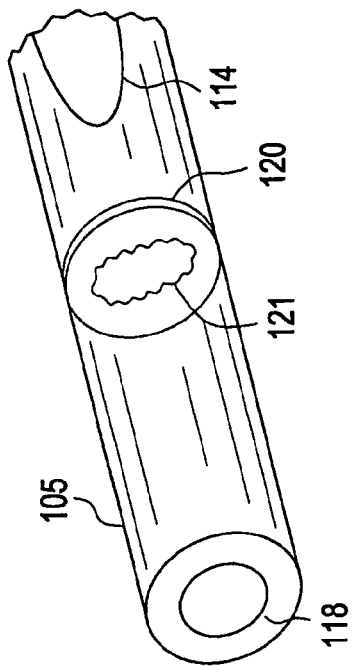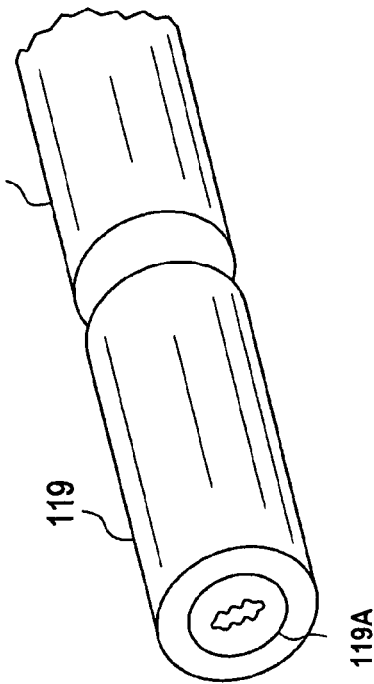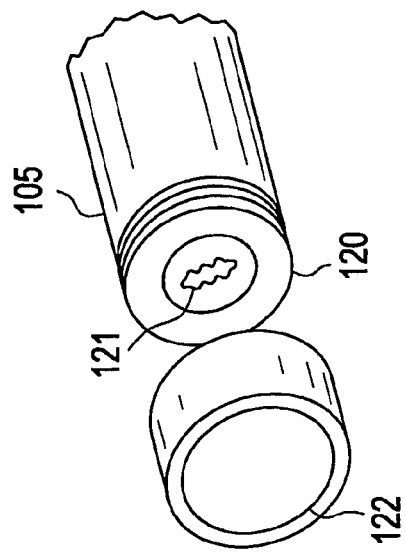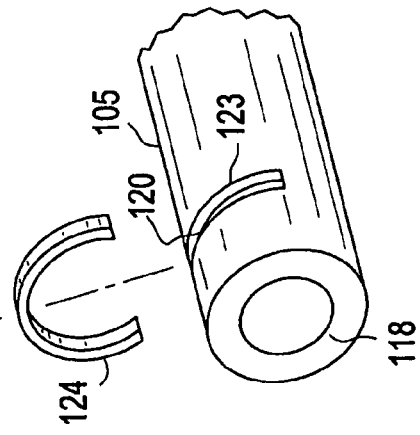

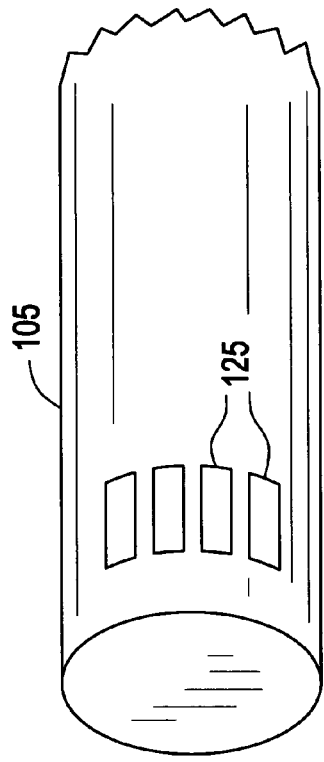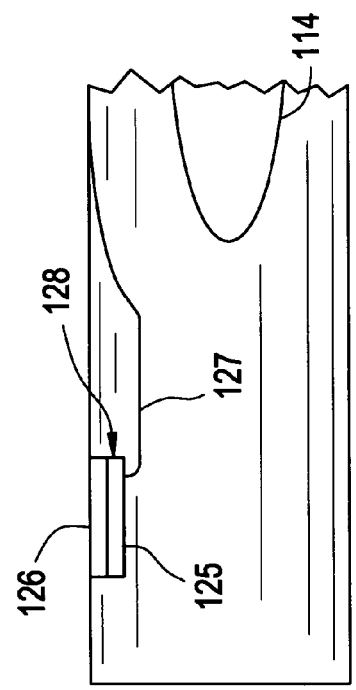

TOOTHBRUSH

The present application claims priority from U.S. Provisional Patent Application Nos. 60/634,108, filed Dec. 8, 2004, and 60/647,805, filed Jan. 31, 2005, the contents of which are incorporated by reference herein in their entirety.

BACKGROUND OF THE INVENTION

1. Field of the Invention

The present invention relates to a toothbrush which can project images onto a remote surface for predetermined periods of time.

2. Description of Related Art

Oral hygienists and dentists emphasize that the duration of the tooth brushing process is an important element of ensuring proper cleaning of the teeth. In general, it is often recommended that teeth be brushed for a minimum period of two minutes for this reason.

However, teaching oral hygienic practices to individuals, particularly to children, can be challenging. For example, a child's attention span tends to be short-lived, and they often do not spend the recommended period of time brushing their teeth. In addition, adults often do not spend the recommended time either, due to time constraints or inattention.

Although enticements to brush longer are used by the dental industry—such as flavored toothpaste, toothbrushes in various shapes and colors, these enticements have not been as beneficial as hoped for in keeping the attention of the individual and lengthening the brushing process.

Accordingly, a toothbrush which could assist an individual in determining the passage of time that is spent is brushing their teeth, as well as distracting the individual if it is a child, would be advantageous.

SUMMARY OF THE INVENTION

The present invention relates to a toothbrush which assists an individual in determining the passage of time that is spent brushing their teeth, and which can also distract the individual during this time period.

In one embodiment consistent with the present invention, the toothbrush includes a head assembly having bristles at a proximal end thereof, a base assembly, and a connector which connects the two. The head assembly is removable from the remainder of the toothbrush such that the head assembly can be replaced to preserve the hygienic quality of the toothbrush.

The connector and the base assembly include internal recesses. A battery and light assembly are disposed in internal recesses of the connector and the base assembly. A battery holder which houses at least one battery (such as a Lithium battery) of an appropriate size and capacity to ensure powering of the toothbrush for at least a few hours, is covered by a cap and inserted into the connector. A light bulb acts as a light source and a power button switch turns the power to the light source "ON/OFF". In one embodiment consistent with the present invention, a timing assembly (i.e., a timer connected to the batteries, light source, and switch) is included in the with the battery and light assembly.

The base assembly includes a switch cover through which access to the power switch is allowed. In one embodiment consistent with the present invention, the base assembly also includes a transparent lens portion at the distal end of the toothbrush, through which a light beam from the light source shines through when the switch is turned ON. The lens portion can be clear or of any color desired.

In another embodiment consistent with the present invention, the light beam from the light source can project a picture or icon through the lens portion onto a remote surface. The method of accomplishing this projection can vary, including 1) having the distal portion of the base assembly with the slide therein, press-fitted or screw-fitted onto the base assembly; or 2) having the slide permanently internally disposed in the base assembly; or 3) having a slot disposed in the distal end of the base assembly, into which an individual slide is interchangeable; or 4) having a distal end of the base assembly containing the slide, and securing the slide on the distal end via a flanged cap or end piece, with an aperture, or with a lens portion therein. However, other embodiments would be apparent to one of ordinary skill in the art.

In another embodiment consistent with the present invention, a timer, if included with the toothbrush, is connected to the battery, light source, and ON/OFF switch, and allows the light source to turn on for a predetermined period of time—such as two minutes. If not turned OFF by the switch, the timer would simply turn OFF after that predetermined period of time.

In another embodiment consistent with the present invention, the exterior of base assembly contains at least one indicator light (i.e., an LED) which indicates how long the light source has been ON, and the lights may be of the same or a different color. The lights may turn OFF individually after a predetermined amount of time has passed—i.e., 30 seconds, or may turn ON after a predetermined period of time. The lights are visible via covered apertures in the base assembly.

Finally, the materials used in the toothbrush would primarily include a plastic or composite material for the base assembly and head assembly, connector, cap, battery holder, and cover. A plastic or man-made fiber may be used for the bristles. These materials would be well-known to one of ordinary skill in the art.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

FIG. 1 shows an exploded perspective view of a toothbrush according to one embodiment consistent with the present invention.

FIGS. 2A-2D show partial perspective distal ends views of different embodiments of the toothbrush consistent with the present invention.

FIG. 3A shows a partial perspective distal end view of one embodiment of the toothbrush consistent with the present invention.

FIG. 3B shows a cross-sectional view of a distal end of the toothbrush according to the embodiment shown in FIG. 3A.

DESCRIPTION OF THE INVENTION

The present invention relates to a toothbrush 100 as shown in FIG. 1, which includes a head assembly 101, a connector 102, a cap 103, a battery and light assembly 104, and a base assembly 105.

The head assembly 101 includes an elongated portion, with a head having bristles 107 at a proximal end thereof. The base 108 of the elongated portion of the head assembly 101 includes a cylindrical portion 109 of a smaller diameter than that of the elongated portion. The cylindrical portion 109 has a grooved appearance to enable it to be screwed into the connector 102. However, as one of ordinary skill in the art would realize, other means of fitting the connector 102 with the head assembly 101—such as a press-fit—can be utilized.

The head assembly 101 is removable from the remainder of the toothbrush 100 such that the head assembly 101 can be replaced from time to time to preserve the hygienic quality of the toothbrush 100 (i.e., a new set of bristles 107 is placed on the toothbrush 100).

The connector 102 attaches the head assembly 101 to the base assembly 105. The connector 102 includes an internal recess into which a portion of the battery and light assembly 104 is inserted. The battery and light assembly 104 includes a switch 110 and can also include a timing assembly 111.

The battery and light assembly 104 includes a battery holder 112 which houses at least one battery 113 (such as a Lithium battery) of an appropriate size and capacity to ensure powering of the toothbrush 100 for at least a few hours before replacement is required.

A cap 103 fits over the battery holder 112, in a press-fit, and protects the batteries 113. The cap 103 is inserted into the internal recess of the connector 102, also using a press-fit or other fitting means.

The battery and light assembly 104 includes a power button switch 110 which turns the power to the light source (i.e., bulb) 114 "ON/OFF".

However, in one embodiment of the present invention, a timing assembly 111 (i.e., a timer connected to the batteries 113, light source 114, and switch 110) is included in the toothbrush 100, and thus, there may be no need for an "OFF" switch (since the light turns off after a predetermined period of time).

The battery and light assembly 104 is inserted into an internal recess of the base assembly 105, and when fully inserted, the base assembly 105 can be connected to the connector 102 via a screw-fit or press-fit or any other connecting means.

An aperture 115 with grooved edges is disposed in the base assembly 105, allowing access to the switch 110, which projects through the aperture 115. A switch cover 116 with an engagement member 117 is disposed in the aperture 115, and is made of a thin rubber-like material, which allows the user to easily access and press the switch 110 through the cover 116. However, in an alternative embodiment, this piece 116 may be eliminated, and the switch 110 can be made to project through the base assembly 101 for direct external access by the user.

The base assembly 105 includes a transparent lens portion 118 (see FIG. 2) at the distal end of the toothbrush 100, through which a light beam from the light source 114 shines through when the switch 110 is turned ON. The lens portion 118 can be clear or of any color desired.

In another embodiment consistent with the present invention, the light beam from the light source 114 can project a picture or icon through the lens portion 118 onto a remote surface. The method of accomplishing this projection can vary, and exemplary embodiments are shown in FIGS. 2A-2D.

As shown in FIG. 2A, the base assembly 105 has a distal portion 119 which contains a lens portion as a picture slide 119A having the picture disposed therein. The distal portion 119 can be press-fitted or screw-fitted onto the base assembly 105. When a beam of light from the battery and light assembly 104 is shown through the distal portion 119 and the slide 119A, the resulting image on the slide 119A is projected onto a remote surface. When the user wishes to change the picture slide 119A, the distal portion 119 can be disconnected and another distal portion with a different picture slide connected thereto.

In another embodiment consistent with the present invention, FIG. 2B shows a base assembly 105 including a lens portion 118 disposed at a distal end of the toothbrush 100. A slide 120 with a picture 121 therein, is disposed within the base assembly 105, and secured by flanges or other securing means, so as not to move or slide 120 when it is disposed in the base assembly 105. In this embodiment, the slide 120 is permanently disposed in the base assembly 105. The light beam from the light source 114 would project the image 121 from the slide 120 through the lens portion 118 onto a remote surface.

In yet another embodiment consistent with the present invention, FIG. 2C shows the base assembly 105 including a lens portion 118 disposed at a distal end of the toothbrush 100. A slot 123 is disposed in the distal end, and an individual slide 120 with a picture therein 121 is disposed in the slot 123. The slide 120 is held within the slot 123 by various means, including a spring mechanism, and/or the slot 120 can be covered by (and the slide 120 held in by) a rubber insert 124 the same shape as the slot 123. The user can remove the insert 124 and change the slide 120 within the slot 123 from time to time as the user wishes. As stated above, the light beam from the light source 114 would project the image 121 from the slide 120 through the lens portion 118 onto a remote surface.

In yet another embodiment consistent with the present invention, FIG. 2D shows the base assembly 10S having a distal end where the slide 120 with picture 121 therein, is disposed and secured by any of the securing means mentioned previously (i.e., a flange within the internal recess of the base assembly 105, for example). A flanged cap 122 or end piece, with an aperture, or with a lens portion therein, is provided to secure the slide 120 to the base assembly 105.

Although a number of different embodiments have been described, it would be apparent to one of ordinary skill in the art that other structural designs are possible and well within the skill of one in the art.

As stated above, in one embodiment consistent with the present invention, the battery and light assembly 105 includes a timing assembly 111, which is a timer connected to the battery 113, light source 114, and ON/OFF switch 110. The timer 111 allows the light source 114 to turn on for a predetermined period of time—such as two minutes. If not turned OFF by the switch 110, the timer 111 would simply turn OFF after that predetermined period of time.

However, in another embodiment consistent with the present invention, the exterior of base assembly 105 may contain at least one indicator light 125 (i.e., an LED) which indicates how long the light source 114 has been ON. For example, as shown in FIG. 3A, the base assembly 105 may have four indicator lights 125, each one of the same or a different color, which will light up when the light source 114 is turned ON, and which will turn OFF individually after a predetermined amount of time has passed—i.e., 30 seconds. Thus, after two minutes have passed, the lights 125 will have all turned OFF, indicating to the user that they may discontinue brushing. Of course, the lights 125 can each turn ON after a predetermined period of time, rather than OFF.

Further, since the lights 125 are disposed externally of the base assembly 105, the distal end of the base assembly 105 can be closed.

A side view of the base assembly 105 in FIG. 3B, shows the wires 127 which extend from the timing assembly 111 to the LEDs 125. The LEDs 125 are visible via apertures 128 in the base assembly 105, and may be covered by a transparent cover 126. Of course, one of ordinary skill in the art would recognize that any shape or positioning of indicator lights may be used in the toothbrush device 100 for indicating the passage of time to the user.

Finally, the materials used in the toothbrush would primarily include a plastic or composite material for the base assembly 105 and head assembly 101, connector 103, cap 103, battery holder 112, and cover 116. A plastic or man-made fiber may be used for the bristles 107. These materials would be well-known to one of ordinary skill in the art.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A toothbrush comprising:
a brush head assembly;
a base assembly;
a light source which projects a beam of light from said base assembly externally of said toothbrush;
a lens portion disposed at a distal end of said base assembly; and
a slide disposed in said base assembly, through which said beam projects, said slide having a picture disposed thereon such that said picture is projected externally of the toothbrush.

2. The toothbrush according to claim 1, further comprising: a connector which connects said head assembly to said base assembly.

3. The toothbrush according to claim 1, further comprising: a battery holder disposed in said base assembly, said battery holder which holds at least one battery.

4. The toothbrush according to claim 3, further comprising: a switch which activates said light source.

5. The toothbrush according to claim 4, further comprising: a timer connected to said at least one battery, said light source, and said switch, said timer which activates said switch for a predetermined period of time.

6. The toothbrush according to claim 5, wherein said timer activates said light source for at least 30 seconds.

7. The toothbrush according to claim 6, further comprising: a plurality of indicator lights disposed in said base assembly, which are activated by said timer.

8. The toothbrush according to claim 7, wherein said lights are activated in a predetermined sequence.

9. The toothbrush according to claim 4, further comprising: an aperture disposed in said base assembly, through which said switch protrudes.

10. The toothbrush according to claim 9, further comprising: a cover disposed in said aperture, which allows access to said switch.

11. The toothbrush according to claim 3, further comprising: a cap disposed on said battery.

12. The toothbrush according to claim 1, wherein said lens portion is transparent or has a color.

13. The toothbrush according to claim 1, wherein said slide is disposed in a distal end portion of said base assembly.

14. The toothbrush according to claim 1, wherein said slide is interchangeable.

15. A toothbrush comprising:
a brush head assembly;
a base assembly;
means for connecting/disconnecting said head assembly from said base assembly;
means for projecting a light beam from said base assembly externally of said toothbrush;
means for projecting said light beam for predetermined periods of time; and
a slide having a picture thereon, through which said light beam is projected, such that said picture is projected externally of the toothbrush.

16. A toothbrush comprising:
a brush head assembly;
a base assembly;
a light source disposed in said base assembly, which projects a light beam externally of said toothbrush;
a timer which activates said light source for predetermined periods of time;
and a slide having a picture thereon, through which said light beam is projected, such that said picture is projected externally of the toothbrush.

* * * * *